(12) United States Patent
Huene (10) Patent No.: US 6,520,991 B2
(45) Date of Patent: Feb. 18, 2003

(54) EXPANDABLE IMPLANT FOR INTER-VERTEBRAL STABILIZATION, AND A METHOD OF STABILIZING VERTEBRAE

(76) Inventor: Donald R. Huene, 201 N. Valeria, Fresno, CA (US) 93701

( * ) Notice: Subject to any disclaimer, the term of this patent is extended or adjusted under 35 U.S.C. 154(b) by 110 days.

(21) Appl. No.: 09/827,916

(22) Filed: Apr. 9, 2001

(65) Prior Publication Data

US 2002/0022887 A1 Feb. 21, 2002

Related U.S. Application Data

(63) Continuation-in-part of application No. 09/309,918, filed on May 11, 1999, now Pat. No. 6,214,050.

(51) Int. Cl.$^7$ .................................................. A61F 2/44
(52) U.S. Cl. ................................. 623/17.11; 623/17.16
(58) Field of Search ............................ 623/17.11–17.16

(56) References Cited

U.S. PATENT DOCUMENTS

| | | | |
|---|---|---|---|
| 2,100,570 A | 11/1937 | Saleh | |
| 2,562,419 A | 7/1951 | Ferris | 81/55 |
| 3,846,846 A | 11/1974 | Fischer | 3/1 |
| 4,011,602 A | 3/1977 | Rybicki et al. | 3/1.9 |
| 4,262,665 A | 4/1981 | Roalstad et al. | 128/92 |
| 4,447,915 A | 5/1984 | Weber | 3/1.9 |
| 4,708,132 A | 11/1987 | Silvestrini | 128/92 |
| 4,744,793 A | 5/1988 | Parr et al. | 623/13 |

(List continued on next page.)

FOREIGN PATENT DOCUMENTS

| | | |
|---|---|---|
| FR | 1322067 | 2/1963 |
| FR | 1368021 | 6/1964 |
| GB | 343992 | 3/1931 |
| RU | 1109142 | 8/1984 |

OTHER PUBLICATIONS

MD–111, "Design Rationale and Surgical Technique", Regeneration Tech., Univ. of Fl., Pamphlet.
Surgical Dynamics, "Threaded Fusion Cage" Pamplet.
Abstract SU–662–082.
Abstract SU 1109–142–A.

*Primary Examiner*—David H. Willse
*Assistant Examiner*—Javier G. Blanco
(74) *Attorney, Agent, or Firm*—Liniak, Berenato & White, LLC (57) ABSTRACT

An expandable intervertebral implant for stabilizing adjacent vertebrae includes first and second opposed and operatively connected shells. Each one of the shells has a plurality of engaging members that are interdigitated with a corresponding plurality of engaging members of another of the shells. The implant also includes at least one extrusion opening and a cavity for containing osteogenic material. As one shell is moved relative to the other shell with a threaded actuator operatively connecting the shells, a volume of the cavity decreases and osteogenic material is extruded through the extrusion opening. A cross section of the implant at one or both ends thereof has a curvalinear shoulder for improved support of the vertebrae during bony growth and fusion of the vertebrae.

23 Claims, 3 Drawing Sheets

U.S. PATENT DOCUMENTS

| | | | |
|---|---|---|---|
| 4,789,284 A | 12/1988 | White | 411/50 |
| 4,870,957 A | 10/1989 | Goble et al. | 128/92 |
| 4,963,144 A | 10/1990 | Huene | 606/73 |
| 5,019,080 A | 5/1991 | Hemer | 606/73 |
| 5,026,373 A | 6/1991 | Ray et al. | 606/61 |
| 5,037,422 A | 8/1991 | Hayhurst et al. | 606/72 |
| 5,059,193 A | 10/1991 | Kuslich | 606/61 |
| 5,092,891 A | 3/1992 | Kummer et al. | 623/16 |
| 5,094,563 A | 3/1992 | Carletti | 403/194 |
| 5,129,902 A | 7/1992 | Goble et al. | 606/65 |
| 5,161,916 A | 11/1992 | White et al. | 405/259.6 |
| 5,172,278 A | 12/1992 | Disharodi | 623/17 |
| 5,176,682 A | 1/1993 | Chow | 606/72 |
| RE34,293 E | 6/1993 | Goble et al. | 623/13 |
| 5,306,301 A | 4/1994 | Graf et al. | 623/13 |
| 5,324,308 A | 6/1994 | Pierce | 606/232 |
| 5,390,683 A | 2/1995 | Pisharodi | 128/898 |
| 5,522,899 A | 6/1996 | Michelson | 623/17 |
| 5,531,792 A | 7/1996 | Huene | 623/16 |
| 5,593,409 A | 1/1997 | Michelson | 606/61 |
| 5,609,635 A | 3/1997 | Michelson | 623/17 |
| 5,645,589 A | 7/1997 | Li | 623/16 |
| 5,653,762 A | 8/1997 | Pisharodi | 623/17 |
| 5,658,335 A | 8/1997 | Allen | 623/17 |
| 5,658,336 A | 8/1997 | Pisharodi | 623/17 |
| 5,665,122 A | 9/1997 | Kambin | 623/17 |
| 5,693,100 A | 12/1997 | Pisharodi | 623/17 |
| 5,741,253 A | 4/1998 | Michelson | 606/61 |
| 5,776,199 A | 7/1998 | Michelson | 623/17 |
| 5,782,919 A | 7/1998 | Zdeblick et al. | 623/17 |
| 5,785,710 A | 7/1998 | Michelson | 606/61 |
| 5,800,550 A | 9/1998 | Sertich | 623/17 |
| 6,436,140 B1 * | 8/2002 | Liu et al. | 623/17.11 |

* cited by examiner

EXPANDABLE IMPLANT FOR INTER-VERTEBRAL STABILIZATION, AND A METHOD OF STABILIZING VERTEBRAE

CROSS-REFERENCES TO RELATED APPLICATIONS

This application is a continuation-in-part of application Ser. No. 09/309,918, filed May 11, 1999 now U.S. Pat. No. 6,214,050.

FIELD OF THE INVENTION

The disclosed invention relates generally to surgical implements and methods used in spinal surgery, and more particularly to an expandable implant for stabilization of vertebrae and a method for stabilizing vertebrae.

BACKGROUND

Chronic back pain is one of the most common and perplexing problems facing the field of orthopedic surgery. In addition to patient discomfort, chronic back pain has severe adverse societal impacts including lost income, decreased involvement in family and community life, as well as possible chronic dependence on drugs and/or alcohol. In many cases, back pain can be avoided by preventing relative motion between spinal vertebrae, a therapy commonly referred to as intervertebral stabilization.

Surgical techniques are known for use in intervetebral stabilization. These surgical techniques seek to rigidly join vertebrae separated by a degenerated disk. Ideally, the surgery effectively replaces the vertebra-disk-vertebra combination with a single rigid vertebra. Various surgical techniques have developed which attempt to approach or approximate this ideal.

One technique known in the art is to place either bone or nothing into the space left after removing a damaged disk. Placing nothing in the space allows the space to collapse which may result in damage to the nerves. With this technique, the space may also fill with scar tissue and eventually lead to a reherniation. The use of bone is less than optimal. If the bone is obtained from the patient, additional surgery is required and the bone is of limited availability in its most useful form. If the bone is obtained elsewhere, the bone may lack living bone cells, carry a significant risk of infection, and/or is also limited in supply since it is usually obtained from accident victims. Furthermore, the bone only provides marginal structural support and lacks a means to either stabilize itself against dislodgement, or to stabilize the adjacent vertebrae.

Another technique involves the use of an implant which, acting alone or in combination with bone fragments, replaces the use of bone grafts. The implants are sometimes expandable to contact adjacent vertebrae and achieve vertebral fusion after a sufficient amount of bone growth occurs. While conventional implants can be filled with bone fragments to expedite bone growth, it is believed that the mere presence of the bone fragments is not enough to achieve the rate of bone growth that would be provided if the bone fragments or any other osteogenic material were extruded from the implant during expansion of the implant.

Whether or not bone fragments or other osteogenic material are used, many implants are less than satisfactory for supporting healing vertebrae after implantation. When a circular bore is drilled into the intervertebral disk space and also into adjacent portions of the vertebrae above and below the intervertebral disk space, many prior art implants provide less than fully satisfactory support to the undrilled, rigid outer surface portions of the vertebrae. As a result of this less than fully satisfactory support, more spinal support structures may be needed, or each of the vertebrae may tilt from side to side, eventually causing spinal misalignment.

Those skilled in the art will appreciate that there is a need for an expandable intervertebral implant which is adapted to extrude osteogenic material during its expansion and to expedite the bone growth and fusion process than compared to the prior art. By expediting the bone growth and fasion process, it is possible to reduce the amount of time between surgery and the patient's ability to return to work or perform physically demanding activities.

Those skilled in the art will also appreciate that there is a need for an expandable intervertebral implant which is adapted to expand against cancellous bone tissue surfaces of vertebrae while providing improved support to vertebrae during the bone growth and fusion process. By providing expansion and improved support, it is possible to reduce the risk of spinal misalignment and decrease the need for additional spinal support structures.

The disclosed invention is just such an implant and achieves the advantages and overcomes the disadvantages of the prior art through use of an expandable intervertebral implant. The expandable intervertebral implant of the present invention extrudes osteogenic material during expansion, and includes a curvalinear shoulder for improved support of vertebrae during the bony growth and fusion process.

OBJECTS AND SUMMARY OF THE INVENTION

It is an object of the invention to provide an expandable implant that will extrude osteogenic material during expansion thereof and which will provide improved support of healing vertebrae during the bony growth and fusion process.

It is another object of the invention to provide an expandable implant that will expand against cancellous bone tissue of a vertebrae while providing improved support of a periosteal membrane surface of the vertebrae during the bony growth and fusion process.

It is yet another object of the invention to provide a method of stabilizing first and second vertebrae with respect to one another that will expedite the bony growth and fusion process while reducing the risk of spinal misalignment.

An expandable intervertebral implant pursuant to the present invention is adapted to be inserted at least partially into vertebrae or in between two vertebrae, and is adapted to be secured thereto by expansion. The implant comprises a first shell, a second shell, and at least one extrusion opening. The first shell has a first end and a plurality of engaging members extensible from the implant for engagement with cancellous bone tissue of a vertebra. The engaging members axially extend from the first end. A cross section of the first shell includes at least one curvalinear shoulder for supporting a periosteal surface of a vertebra. The second shell is operatively connected to the first shell and has a second end with at least one bore bearing surface engageable with the engaging members. A cross section of the second shell including at least one curvalinear shoulder for supporting a periosteal surface of a vertebra. The first and second shells cooperate to form a cavity delimited by inner surfaces thereof. There is at least one extrusion opening in at least one of the first and second shells. Movement of the second shell with respect to the first shell causes expansion of the implant and at least partial extrusion of material contained in the cavity through the extrusion opening.

An expandable intervertebral implant pursuant to the present invention is adapted to be inserted at least partially into a bore drilled between two adjacent vertebrae to expose cancellous bone tissue within each of the two vertebrae, and is also adapted to be secured to the vertebrae by expansion. The implant comprises first and second shells and first, second and third axes. The first shell has a first end and a plurality of engaging members extensible from the implant for engagement with the cancellous bone tissue of a vertebra. The engaging members axially extend from the first end. A cross section of the first shell includes at least one curvalinear shoulder for supporting a periosteal surface of a vertebra. A second shell is operatively connected to the first shell and has a second end with at least one bearing surface engageable with the engaging members. A cross section of the second shell includes at least one curvalinear shoulder for supporting a periosteal surface of a vertebra. The first axis extends between the first and second ends, while the second axis extends perpendicular to the first axis. The third axis extends perpendicular to the first and second axes, wherein the second axis has a length greater than a diameter of the bore and the third axis has a length less than the diameter of the bore.

A method for stabilizing first and second vertebrae with respect to one another pursuant to the present invention comprises the following steps. A bore is formed between two vertebrae to expose cancellous bone tissue in at least one vertebra. At least one expandable intervertebral implant containing osteogenic material is provided. The implant has first, second and third axes and first and second opposed shells. A cross section of the implant has at least one curvalinear shoulder for supporting a periosteal membrane of one of the two adjacent vertebrae. The first axis extends between the ends. The second axis extends perpendicular to the first axis and has a length greater than a diameter of the bore. The third axis extends perpendicular to the first and second axes and has a length equal to or less than the diameter of the bore. At least one of the first and second shells has engaging members extensible from the implant for engagement with the cancellous bone tissue, wherein the engaging members extend axially from an end of the at least one shell. The implant is inserted in the bore so that the curvalinear shoulder bears against and supports the periosteal membrane. The implant is expanded. An osteogenic material is extruded from the implant during expansion thereof.

These and other objects of the present invention will become apparent from the following detailed description and independent claims.

The invention may be best understood with reference to the accompanying drawings wherein an illustrative embodiment is shown.

DETAILED DESCRIPTION

Expandable intervertebral implant I, as best shown in FIGS. 1–6, has a first shell 2 operatively connected to a second shell 5. Movement of second shell 5 with respect to first shell 2 effects radial outward expansion of implant I along with extrusion of osteogenic material through extrusion openings 8. The osteogenic material may be bone material or any other substance capable of expediting or facilitating bone growth. Implant I has a configuration adapted to provide improved support to rigid portions of a vertebrae at a surface of a periosteal membrane.

Figure 1:
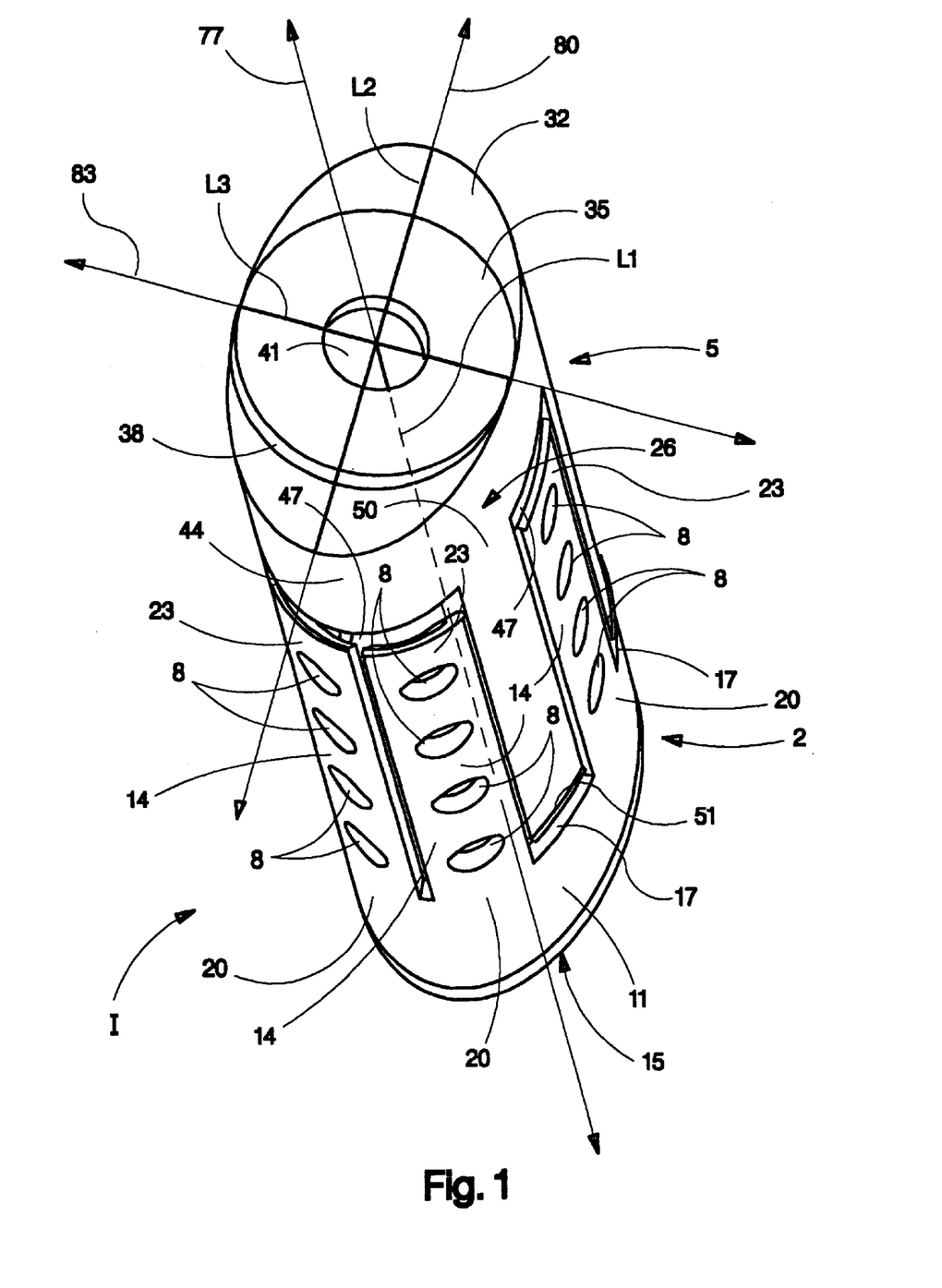
FIG. 1 is a perspective view of the inventive implant.

As best illustrated in FIG. 1, first shell 2 has a first end 11, a plurality of circumferentially spaced engaging members 14 that axially extend from first end 11, and a plurality of extrusion openings 8 formed in engaging members 14. First end 11 has a smooth, essentially uninterrupted, concave-shaped surface 15. A cross-section of concave-shaped surface 15 is oval. First end 11 also has a plurality of circumferentially spaced bearing surfaces 17 that alternate with attachment points 20 of engaging members 14. Preferably, first shell 2 has six engaging members 14 and first end 11 has four bearing surfaces 17. Engaging members 14 are arcuately shaped, i.e., a cross-section of each engaging member 14 taken orthogonal to the axial extension direction describes an curve or arc. Bearing surfaces 17 and distal ends 23 of engaging members 14 are beveled.

As best shown in FIG. 1, second shell 5 has a second end 26 and a plurality of circumferentially spaced engaging members 29 axially extending from second end 26. Second end 26 has an oval planar surface 32 with a raised cylindrical portion thereupon 35. Raised cylindrical portion 35 has external threads 38 for engaging an installation tool. A hole 41 is formed through raised cylindrical portion 35 for receiving a fastener for connecting first and second shells 2, 5. Oval planar surface 32 is oriented orthogonal to a smooth, essentially uninterrupted, curvalinear surface 44 having an oval cross-section. Second end 26 also has a plurality of bearing surfaces 47 that alternate with attachment points 50 of engaging members 29. Preferably, second shell 5 has four engaging members 29 and second end 26 has four bearing surfaces 47. Similar to first shell 2, bearing surfaces 47 and distal ends 51 of engaging members 29 of second shell 5 are beveled.

Osteogenic material may be placed into a cavity that is defined by inner surfaces of first and second shells 2, 5. As second shell 5 is moved toward first shell 2, the cavity decreases in volume and the osteogenic material is extruded through extrusion openings 8. The osteogenic material promotes bony growth and eventual fusion of vertebrae.

Figures 3, 4, 5:
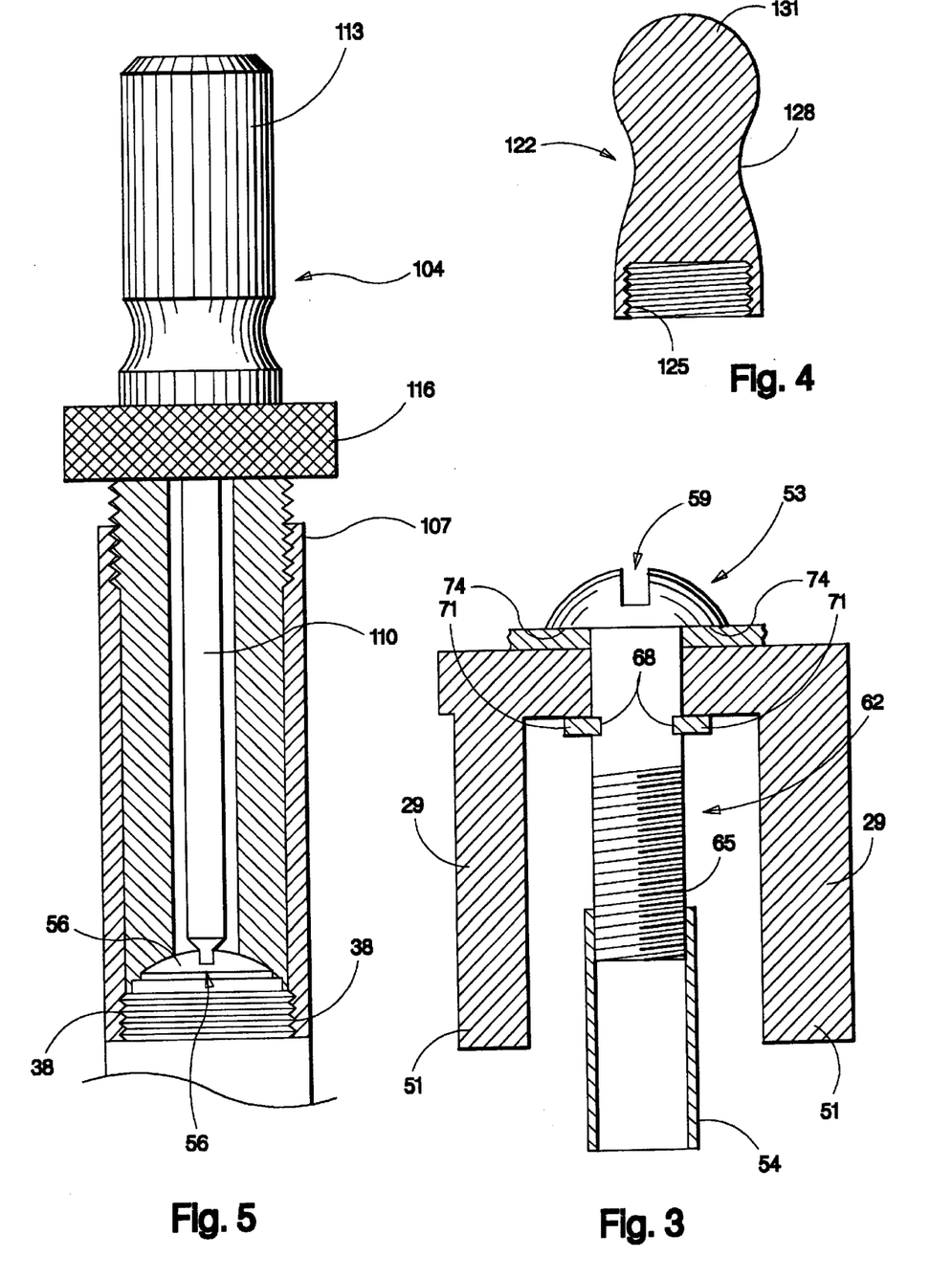
FIG. 3 is a cross-sectional view of an actuator installed inside the second shell of the inventive implant.
FIG. 4 is a cross-sectional view of an extension for use with the inventive implant.
FIG. 5 is a cross-sectional view of a tool for use with the inventive implant.

As best illustrated in FIG. 3, movement and operative connection of first and second shells 2, 5 is preferably effected by an actuator 53 that is threadedly connected to an internally threaded post 54 inside first shell 2. Actuator 53 has a head 56 with a slot 59 formed therein and a shank 62 having external threads 65 formed about a lower half thereof. A groove 68 is formed in shank and receives clip 71, thereby keeping actuator 53 from coming apart from second shell 5 during installation and manipulation of implant I. Actuator 53 extends through hole 41 in second shell 5, where head 56 is retained upon surface 74.

As best shown in FIG. 1, engaging members 14 of first shell 2 are interdigitated with engaging members 29 of second shell 5 and each engaging member 14, 29 bears upon its corresponding bearing surface 47, 17. As a user applies torque in one direction to actuator 53, actuator 53 threadedly engages the threaded post 54 of first shell 2, causing second shell 5 to move toward first shell 2. Application of torque in an opposite direction causes second shell 5 to move away from first shell 2. Thus, a surgeon may freely adjust a relative position of first shell 2 with respect to second shell 5. As second shell 5 is moved toward first shell 2, engaging members 14 of first shell 2 are urged radially outwardly by bearing surfaces 47 of second shell 5. Similarly, engaging members 29 of second shell are urged radially outward by bearing surfaces 17 of first shell 2. Beveled distal ends 23, 51 and beveled bearing surfaces 47, 17 ease this radial outward movement of engaging members 14, 29. A combination of the radial outward movement of engaging members 14, 29 causes implant I to become radially expanded.

Figure 2:
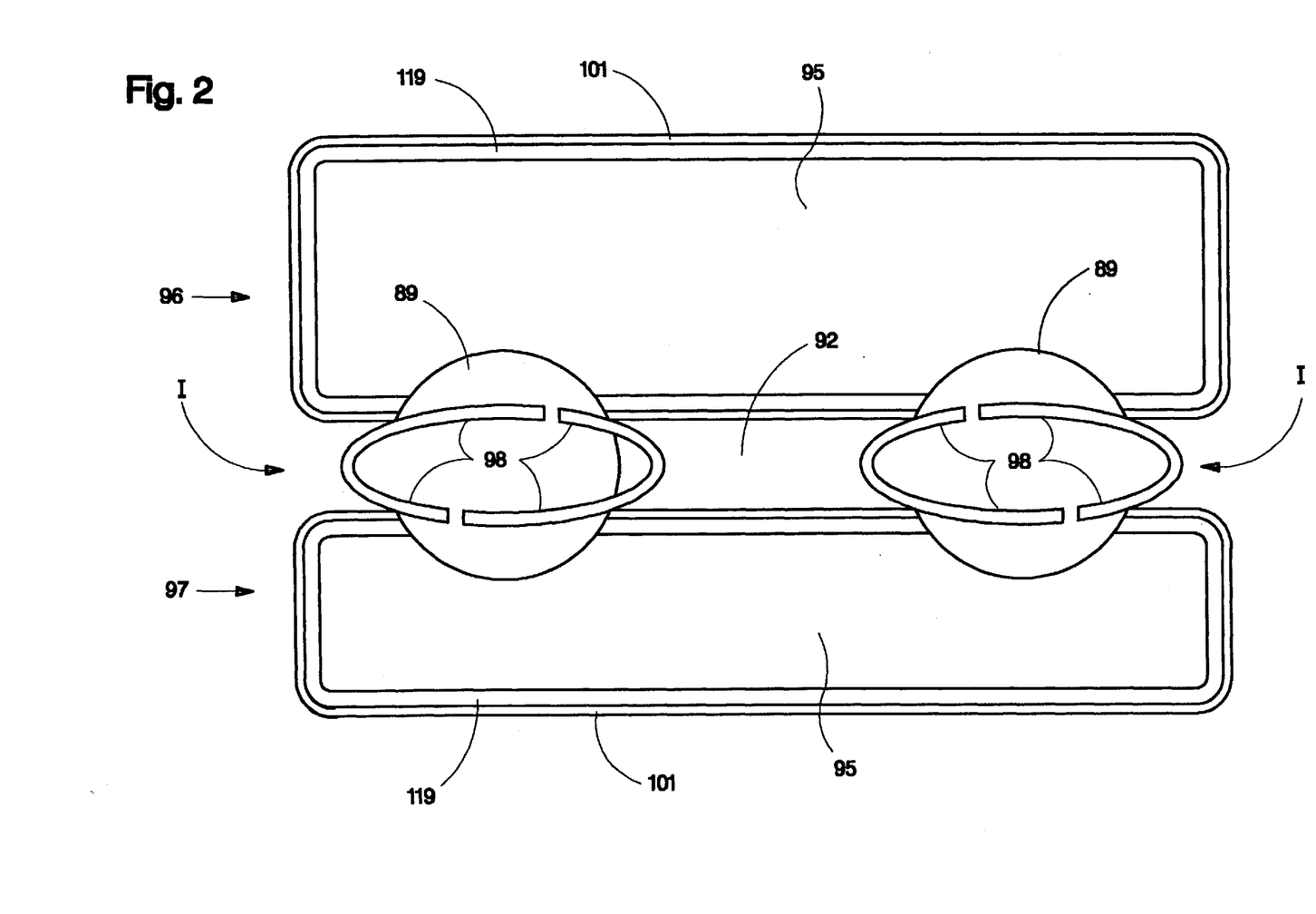
FIG. 2 is a cross-sectional view of two of the inventive implants as inserted into an implant site between adjacent vertebrae.

As best illustrated in FIGS. 1–2, the configuration of implant I may also be described with reference to first, second, and third axes 77, 80, 83. First axis 77 (partially shown as a hidden line in FIG. 1) extends between first and second ends 11, 26. Second axis 80 extends perpendicular to first axis 77 and third axis 83 extends perpendicular to both first and second axes 77, 80. Third axis 83 has a length L3 less than a diameter of surgical bore 89 allowing implant I to be inserted into intervertebral space 92 and expanded against cancellous bone tissue 95 of first and second vertebrae 96, 97. Because second axis 80 has a length L2 greater than the diameter of bore 89, curvalinear shoulders 98 jut out to either side of implant I to support surfaces of periosteal membrane 101 over an rigid outer bony later 119 of vertebrae 96, 97, as best shown in FIG. 2. In such a configuration, outer surfaces of first and second shells 2, 5 cooperate to form an ellipsoid, of which second end 26 is generally planar and oriented orthogonal to axis 77. Thus, a cross-section of implant I taken at a point along axis 77 has an oval shape. One skilled in the art will appreciate that implant I need not have an ellipsoid shape or an oval cross-section. In this embodiment, the cross-section need only describe at least one curvilinear shoulder 98 for supporting rigid outer bony layer 119 of vertebrae 96, 97 at a surface of periosteal membrane 101.

While various dimensions can be provided, depending on the intended use of each implant I, preferred dimensions permit use of implant I as an intervertebral stabilization device. First and second shells 2, 5, in this regard, are provided with dimensions that permit insertion of implant I between two vertebrae 96, 97 and radial expansion of engaging members 14, 29 in order to provide stabilization of vertebrae 96, 97 with respect to one another. The exact dimensions will depend on a size of intervertebral space 92 in a patient. For example, the dimensions will be correspondingly smaller for implants I designed for pediatric patients than those designed for adult patients. Exemplary dimensions for an adult spinal patient include a first axis length L1 of about 20 to 26 millimeters. The unexpanded third axis length L3 for an implant I designed for an adult patient preferably is about 9 to 10 millimeters, with a diametric expansion of about 8 to 10 millimeters being provided for outward movement of engaging members 14,29.

With reference to FIG. 5, a tool 104 may be used with implant I for purposes of inserting or otherwise manipulating implant I. Tool 104 should be capable of turning actuator 53 to effect expansion or contraction of implant I while actuator 53 is engaged with implant I. A preferred tool 104 is disclosed in my U.S. Pat. No. 5,531,792, the disclosure of which is incorporated herein by reference.

Tool 104 has a sleeve 107 which is internally threaded to engage external threads 38 of raised cylindrical portion 35. A screw driver portion 110 passes through sleeve 107 and engages head 56 of actuator 53 to permit manual turning of actuator 53 while sleeve 107 remains engaged to external threads 38. Sleeve 107 allows implant I to be manipulated as a unit to achieve a desired position in an implant site, while screw driver portion 110 facilitates movement of second shell 5 for purposes of selectively expanding or contracting implant I. Screw driver portion 110 preferably is connected to a screw driver handle 113 which provides a mechanical advantage when screw driver portion 110 is turned. A knurled ring 116 is rigidly connected to sleeve 107 to facilitate turning of sleeve 107 with respect to external threads 38, for example, when connecting or disconnecting tool 104 from implant I.

Each of first and second shells 2, 5 and actuator 53 are preferably made of biocompatible material, such as surgical grade titanium or surgical grade stainless steel. The osteogenic material is preferably bone material.

With reference to FIGS. 1 and 3, the implant I may be assembled by inserting actuator 53 through hole 41 of second end 26 and installing clip 71 within groove 68. Engaging members 29 of second shell 5 are brought into interdigital orientation relative to engaging members 14 of first shell 2, and actuator 53 is rotated so that threads 65 engage the internally threaded post 54 in first shell 2. Actuator 53 is further rotatably inserted within the internally threaded post 54 so as to snugly fit beveled distal ends 23, 51 of engaging members 14, 29 against corresponding beveled bearing surfaces 47, 17, but not so much as to cause engaging members 14, 29 to be urged or extended radially outwardly. Implant I is thus in the non-expanded condition, suitable for insertion into a previously prepared implantation site.

Implant I may be used to perform a method of stabilizing vertebrae. First, a surgical bore 89 is drilled into an intervertebral disk space 92, as best shown in FIG. 2. Surgical bore 89 should be at least partially drilled into vertebrae 96, 97 in order to expose cancellous bone tissue 95. Tool 104 is then attached to implant I as explained above, and implant I positioned inside surgical bore 89.

As best shown in FIGS. 1–2, the unexpanded implant I provides improved support of vertebrae 96, 97 during the bony growth and fusion process. Each of first and second vertebrae 96, 97 have a periosteal membrane 101 which covers a rigid outer bony layer 119, which in turn encloses cancellous bone tissue 95, otherwise known as spongy bone tissue. Implant I is configured such that curvalinear shoulders 98 are well suited to support rigid portions of vertebrae 96, 97 at surfaces of periosteal membrane 101. Because vertebrae 96, 97 are supported in such a manner, they are less prone to rock, tilt or shift, thus reducing the risk of spinal misalignment, and decreasing the need for additional vertebral support structures. Once placed within surgical bore 89, implant I should be carefully positioned so that curvalinear shoulders 98 bear against and support rigid portions of vertebrae 96, 97 at periosteal membrane 101.

As best illustrated in FIGS. 1 and 5, implant I may be expanded by passing screw driver portion 110 through sleeve 107, and allowing it to engage slot 59. Handle 113 is then rotated so that second shell 5 is moved toward first shell 2. As first and second shells 2, 5 come closer together, bearing surfaces 17, 47 urge engaging members 29, 14 radially outward so as to engage cancellous bone tissue 95 and effect radial expansion of implant 1. The movement of second shell 5 toward first shell 2 also effects a reduction in volume of the cavity contained therein. As a result, osteogenic material is extruded through extrusion openings 8.

Rotation of handle 113 is stopped once the desired degree of radial expansion is achieved. If implant I is over expanded, screw driver handle 113 may be rotated in the opposite direction to move first and second shells 2, 5 apart, thus radially contracting implant I. Once the surgeon determines that a satisfactory degree of expansion is attained, screw driver portion 110 may be removed from sleeve 107, and sleeve 107 unscrewed from threads 38 to remove tool 104 from implant I.

It should be appreciated that smooth surfaces 15, 44 permit implant I to be inserted and installed with minimal damage, if any, to surrounding vertebrae 96, 97. The construction of implant I permits engaging members 14, 29 to extend gradually radially outwardly, thereby reducing the risk of overstressing surrounding vertebrae 96, 97. Compressing cancellous bone tissue 95 by expansion of implant I causes implant L to be secured and fixed within surgical bore 89. During a necessary period of time for healing of vertebrae 96, 97, osteogenic material in intervertebral space 92, in the implant I cavity, and against cancellous bone tissue 95, will promote bony growth. Once bony growth is substantially achieved, vertebrae 96, 97 will have become fused together.

In treating some patients (e.g., scoleosis patients, patients with spinal curvature, and/or trauma patients), it may be desirable to connect implant I to a spinal stabilization rod. Such rods are well known in the art. As shown in FIG. 4, the implant I can be provided with an extension 122. Extension 122 includes internal threads 125 adapted to engage external threads 38 of raised cylindrical portion 35 and thus can be used to secure extension 122 to implant I. Extension 122 further includes a neck portion 128 and a ball 131. Ball 131 and neck portion 128 can be engaged and locked to a suitable spinal stabilization rod in a trailer hitch-like manner. Alternatively, other engagement and locking means can be used to connect the rod and implant I.

While the expandable intervertebral implant and method of the present invention are particularly well-suited for use in stabilizing vertebrae, it is understood that the invention is not limited to such use. The inventive implant can be modified and/or used to stabilize other bones, as one having ordinary skill in the art would readily appreciate from the instant disclosure.

Moreover, while this invention has been described as having a preferred design, it is understood that the invention is not limited to the illustrated and described features. To the contrary, the invention is capable of further modifications, usages, and/or adaptations following the general principles of the invention and therefore includes such departures from the present disclosure as come within known or customary practice in the art to which the invention pertains, and as may be applied to the central features set forth above, and which fall within the scope of the appended claims.

I claim:

1. An expandable intervertebral implant adapted to be inserted at least partially into vertebrae or in between two vertebrae, and adapted to be secured thereto by expansion, comprising:

a first shell having a first end and a plurality of engaging members extensible from the implant for engagement with cancellous bone tissue of a vertebra, said engaging members axially extending from said first end, a cross section of said first shell including at least one curvalinear shoulder for supporting a periosteal surface of a vertebra;

a second shell operatively connected to said first shell and having a second end with at least one bearing surface engageable with said engaging members, a cross section of said second shell including at least one curvalinear shoulder for supporting a periosteal surface of a vertebra, said first and second shells cooperating to form a cavity delimited by inner surfaces thereof; and at least one extrusion opening in at least one of said first and second shells, wherein movement of said second shell with respect to said first shell causes expansion of the implant and at least partial extrusion of material contained in the cavity through said extrusion opening.

2. The implant according to claim 1, wherein:

said cavity has a volume that varies depending upon a position of said first shell with respect to said second shell.

3. The implant according to claim 1, further comprising:

an actuator adapted to move said second shell with respect to said first shell.

4. The implant according to claim 3, wherein:

said actuator has a third end threadedly connected to at least one of said first and second shells, said actuator being responsive to torque applied in a first predetermined direction to move said second shell toward said first shell and expand the implant thereby at least partially extruding material contained within said cavity.

5. The implant according to claim 4, wherein:

said actuator is responsive to torque in a second predetermined direction to cause said second shell to move away from said first shell and radially contract the implant.

6. The implant according to claim 1, wherein:

an osteogenic material is contained within said cavity and is extruded during expansion of the implant.

7. The implant according to claim 1, wherein:

said at least one bearing surface engages said engaging members and urges said engaging members radially outward to effect expansion of the implant and extrusion of the material contained within said cavity when said second shell is moved with respect to said first shell.

8. The implant according to claim 1, wherein:

said first shell includes a plurality of bearing surfaces on said first end.

9. The implant according to claim 8, wherein:

said second shell includes a plurality of engaging members axially extending from said second end, said engaging members of said first shell being interdigitated with said engaging members of said second shell.

10. The implant according to claim 9, wherein:

said at least one bearing surface of said second shell urges said engaging members of said first shell radially outward and said plurality of bearing surfaces of said first shell urge said engaging members of said second shell radially outward to effect expansion of the implant when said second shell is moved with respect to said first shell.

11. The implant according to claim 10, wherein said engaging members of said first and second shells are circumferentially spaced about a first axis extending from said first end to said second end.

12. The implant according to claim 9, wherein:

said engaging members of said first and second shells have a common length.

13. The implant according to claim 10, wherein:

each of said engaging members of said first and second shells has a beveled distal end.

14. The implant according to claim 13, wherein:
said bearing surfaces of said first and second shells are beveled so that movement of said second shell toward said first shell effects effects radially outward extension of said engaging members of said first and second shells.

15. An expandable intervertebral implant adapted to be inserted at least partially into vertebrae or in between two vertebrae, and adapted to be secured thereto by expansion, comprising:
a first shell having a first end and a plurality of engaging members extensible from the implant for engagement with cancellous bone tissue of a vertebra, said engaging members axially extending from said first end, a cross section of said first shell including at least one curvalinear shoulder for supporting a periosteal surface of a vertebra;
a second shell operatively connected to said first shell and having a second end with at least one bearing surface engageable with said engaging members, cross section of said second shell including at least one curvalinear shoulder for supporting a periosteal surface of a vertebra, said first and second shells cooperating to form a cavity delimited by inner surfaces thereof;
an actuator adapted to move said second shell with respect to said first shell, said actuator extending through a bore in one of said first and second shells and having a head and a third end, said head bearing against said one shell, said third end threadedly connected to another of said first and second shells; and
at least one extrusion opening in at least one of said first and second shells, wherein movement of said second shell with respect to said first shell causes expansion of the implant and at least partial extrusion of material contained in the cavity through said extrusion opening.

16. An expandable intervertebral implant adapted to be inserted at least partially into a bore drilled between two adjacent vertebrae to expose cancellous bone tissue within each of the two vertebrae, and adapted to be secured to the vertebrae by expansion, comprising:
a first shell having a first end and a plurality of engaging members extensible from the implant for engagement with cancellous bone tissue of a vertebra, said engaging members axially extending from said first end, a cross section of said first shell including at least one curvalinear shoulder for supporting a periosteal surface of a vertebra;
a second shell operatively connected to said first shell and having a second end with at least one bearing surface engageable with said engaging members, cross section of said second shell including at least one curvalinear shoulder for supporting a periosteal surface of a vertebra;
a first axis extending between said first and second ends;
a second axis extending perpendicularly to said first axis; and
a third axis extending perpendicularly to said first and second axes, wherein said second axis has a length greater than a diameter of the bore and said third axis has a length less than the diameter of the bore.

17. The implant according to claim 16, further comprising:
at least one extrusion opening in at least one of said first and second shells, said first and second shells cooperating to form a cavity delimited by inner surfaces thereof, wherein movement of said second shell with respect to said first shell effects expansion of the implant and at least partial extrusion of material contained in the cavity through said extrusion opening.

18. A method for stabilizing first and second vertebrae with respect to one another, said method comprising the steps of:
forming a bore between two vertebrae to expose cancellous bone tissue in at least one vertebra;
providing at least one expandable intervertebral implant containing osteogenic material, the implant having first, second and third axes and first and second opposed shells, a cross section of the implant having at least one curvalinear shoulder for supporting a periosteal membrane of one of the two adjacent vertebrae, the first axis extending between the ends, the second axis extending perpendicular to the first axis and having a length greater than a diameter of the bore, the third axis extending perpendicular to the first and second axes and having a length equal to or less than the diameter of the bore, at least one of the first and second shells having engaging members extensible from the implant for engagement with the cancellous bone tissue, the engaging members extending from an end of the at least one shell;
inserting the implant in the bore so that the curvalinear shoulder bears against and supports the periosteal membrane;
expanding the implant.

19. The method of claim 18, including the step of:
effecting expansion of the implant by moving the second shell with respect to the first shell and thereby extending the engaging members toward the cancellous bone tissue.

20. The method of claim 18, including the further step of:
extruding an osteogenic material from the implant during expansion thereof.

21. An expandable intervertebral implant adapted to be inserted at least partially into a bore drilled into an intervertebral disk space between two adjacent vertebra to expose cancellous bone tissue, and adapted to be secured to the vertebrae by expansion, comprising:
first and second opposed and operatively connected shells, each of said shells having an end, at least one of said shells have a plurality of engaging members engageable with the cancellous bone tissue, said engaging members axially extending from said at least one shell and being radially extensible from the implant, a cross section of at least one of said ends having a curvalinear shoulder for supporting a rigid portion of one of the vertebrae;
at least one extrusion opening in at least one of said shells, wherein movement of second shell with respect to said first shell effects radial extension of said engaging members and thereby at least partially extruding osteogenic material through said extrusion opening.

22. An expandable intervertebral implant adapted to be inserted at least partially into a bore drilled between two adjacent vertebrae to expose cancellous bone tissue within each of the two vertebrae, and adapted to be secured to the vertebrae by expansion, comprising:
a first shell having a first end, a plurality of engaging members radially extensible from the implant, said engaging members axially extending from said first end, said first end including a plurality of bearing surfaces, a cross section of said first shell including at least one curvalinear shoulder for supporting a periosteal surface of a vertebra;

a second shell operatively connected to said first shell and having a second end and a plurality of engaging members, said second end having a plurality of bearing surfaces engageable with said engaging members of said first shell, said engaging members of said second shell engageable with said bearing surfaces of said first end, a cross section of said second shell including at least one curvalinear shoulder for supporting a periosteal surface of a vertebra;

a first axis extending between said first and second ends;

a second axis extending perpendicular to said first axis; and a third axis extending perpendicular to said first and second axes, wherein said second axis has a length greater than a diameter of the bore and said third axis has a length less than the diameter of the bore, wherein said bearing surfaces of said first and second ends urge said engaging members of said second and first shells radially outward for contact with cancellous bone tissue.

23. An expandable intervertebral implant adapted to be inserted at least partially into a bore drilled into an intervertebral disk space between two adjacent vertebra to expose cancellous bone tissue, and adapted to be secured to the vertebrae by expansion, comprising:

first and second opposed and operatively connected shells, each of said shells having an end and a curvalinear outer surface axially extending therefrom, at least one of said curvalinear outer surfaces comprising a plurality of engaging members engageable with the cancellous bone tissue, said engaging members being extensible from the implant, said curvalinear outer surfaces cooperating to form an ellipsoid surface for supporting a rigid portion of one of the vertebrae;

at least one extrusion opening in at least one of said shells, wherein movement of second shell with respect to said first shell effects extension of said engaging members from the implant thereby expanding the implant and at least partially extruding osteogenic material contained within the implant through said extrusion opening.

* * * * *